United States Patent
Hazelton et al.

(10) Patent No.: US 12,268,361 B2
(45) Date of Patent: Apr. 8, 2025

(54) IMAGING SYSTEMS AND METHODS OF USE

(71) Applicant: INTUITIVE SURGICAL OPERATIONS, INC., Sunnyvale, CA (US)

(72) Inventors: Andrew J. Hazelton, San Carlos, CA (US); Lucas S. Gordon, San Jose, CA (US); Candice Murray, Palo Alto, CA (US); Randall L. Schlesinger, San Mateo, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 17/943,516

(22) Filed: Sep. 13, 2022

(65) Prior Publication Data

US 2023/0000326 A1 Jan. 5, 2023

Related U.S. Application Data

(63) Continuation of application No. 16/955,246, filed as application No. PCT/US2018/054586 on Oct. 5, 2018, now Pat. No. 11,478,138.

(Continued)

(51) Int. Cl.
*A61B 1/005* (2006.01)
*A61B 1/00* (2006.01)
(Continued)

(52) U.S. Cl.
CPC .......... *A61B 1/005* (2013.01); *A61B 1/00062* (2013.01); *A61B 1/04* (2013.01);
(Continued)

(58) Field of Classification Search
CPC ............ A61B 1/00114; A61B 1/00119; A61B 1/00135; A61B 1/005; A61B 1/015;
(Continued)

(56) References Cited

U.S. PATENT DOCUMENTS 6,380,732 B1  4/2002  Gilboa
6,389,187 B1  5/2002  Greenaway et al.
(Continued)

FOREIGN PATENT DOCUMENTS

JP      2001008885 A    1/2001
WO   WO-2014107247 A1   7/2014
(Continued)

OTHER PUBLICATIONS

International Preliminary Report on Patentability for Application No. PCT/US2018/054586 mailed on Jul. 2, 2020, 12 pages.
(Continued)

*Primary Examiner* — Aaron B Fairchild
*Assistant Examiner* — Stephen Floyd London
(74) *Attorney, Agent, or Firm* — Haynes & Boone, LLP.

(57) ABSTRACT

A system may comprise a catheter including a wall having an inner surface defining a main lumen. The system may also comprise a device including an elongate flexible shaft configured to be slideably inserted within the catheter main lumen and a structure disposed around an outer surface of the elongate flexible shaft. The structure may be configured to engage with a plurality of flat surfaces comprising a portion of the inner surface to prevent rotation of the device within the main lumen.

14 Claims, 10 Drawing Sheets

Related U.S. Application Data

(60) Provisional application No. 62/607,769, filed on Dec. 19, 2017.

(51) Int. Cl.

| | | |
|---|---|---|
| *A61B 1/04* | (2006.01) | |
| *A61B 1/05* | (2006.01) | |
| *A61B 1/06* | (2006.01) | |
| *A61B 1/07* | (2006.01) | |
| *A61B 1/12* | (2006.01) | |
| *B25J 9/16* | (2006.01) | |

(52) U.S. Cl.
CPC .............. *A61B 1/05* (2013.01); *A61B 1/0684* (2013.01); *A61B 1/07* (2013.01); *A61B 1/12* (2013.01); *B25J 9/1689* (2013.01)

(58) Field of Classification Search
CPC .............. A61B 5/6852; A61B 1/00057; A61B 1/00066; A61B 1/00073; A61B 1/00075; A61B 1/00124; A61B 1/00128; A61B 1/0014; A61B 1/0125; A61B 1/018; A61M 25/0032; A61M 25/0097; A61M 2039/1088; A61M 25/0625; A61M 2025/09125; A61M 2025/09175; A61M 2025/09183
USPC ........................................................ 600/128
See application file for complete search history.

(56) References Cited

U.S. PATENT DOCUMENTS

| | | | |
|---|---|---|---|
| 7,772,541 B2 | 8/2010 | Froggatt et al. | |
| 8,622,896 B1* | 1/2014 | Termanini ............ | A61B 1/0684 600/179 |
| 8,900,131 B2 | 12/2014 | Chopra et al. | |
| 9,452,276 B2 | 9/2016 | Duindam et al. | |
| 10,542,868 B2 | 1/2020 | Gordon et al. | |
| 2003/0004400 A1* | 1/2003 | Smith .................... | A61B 1/018 600/153 |
| 2004/0097965 A1* | 5/2004 | Gardeski ........... | A61M 25/0021 606/129 |
| 2005/0209631 A1* | 9/2005 | Galdonik ........ | A61M 25/09025 606/108 |
| 2006/0013523 A1 | 1/2006 | Childers et al. | |
| 2007/0038213 A1* | 2/2007 | Machiya ............ | A61B 18/1492 606/45 |
| 2008/0208006 A1 | 8/2008 | Farr | |
| 2008/0243162 A1* | 10/2008 | Shibata .............. | A61B 17/3417 606/185 |
| 2008/0319376 A1 | 12/2008 | Wilcox et al. | |
| 2009/0024141 A1* | 1/2009 | Stahler .................... | A61B 34/71 606/130 |
| 2009/0281388 A1* | 11/2009 | Ito ......................... | A61B 1/0055 600/121 |
| 2011/0230716 A1* | 9/2011 | Fujimoto ........... | G02B 27/0006 600/121 |
| 2011/0301414 A1* | 12/2011 | Hotto .................. | A61B 1/00082 600/114 |
| 2012/0238796 A1 | 9/2012 | Conlon | |
| 2013/0066304 A1 | 3/2013 | Belson et al. | |
| 2014/0107496 A1* | 4/2014 | Hellstrom ............ | A61B 5/0086 600/478 |
| 2015/0182108 A1* | 7/2015 | Fukuda .............. | A61B 1/00091 600/157 |
| 2016/0073861 A1* | 3/2016 | Kaneko .............. | G02B 23/2476 600/125 |
| 2016/0095508 A1* | 4/2016 | Terliuc ............... | A61B 1/00057 134/21 |
| 2016/0213239 A1* | 7/2016 | Fujii .................. | A61B 1/00163 |
| 2017/0086938 A1 | 3/2017 | Mak et al. | |
| 2017/0196651 A1 | 7/2017 | Jones et al. | |
| 2017/0231475 A1 | 8/2017 | Mcweeney et al. | |
| 2017/0238795 A1 | 8/2017 | Blumenkranz et al. | |
| 2017/0266410 A1* | 9/2017 | Farrell .................... | A61M 1/84 |
| 2018/0192858 A1* | 7/2018 | Konstorum ............ | A61B 90/70 |
| 2019/0029508 A1 | 1/2019 | Tabata et al. | |
| 2019/0070395 A1* | 3/2019 | Govari .................... | A61B 1/07 |
| 2020/0323424 A1 | 10/2020 | Hazelton et al. | |
| 2020/0383750 A1 | 12/2020 | Kemp et al. | |

FOREIGN PATENT DOCUMENTS

| | | |
|---|---|---|
| WO | WO-2016025465 A1 | 2/2016 |
| WO | WO-2017210333 A1 | 12/2017 |

OTHER PUBLICATIONS

International Search Report and Written Opinion for Application No. PCT/US2018/054586, mailed on Feb. 14, 2019, 17 pages (ISRG10810/PCT).

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

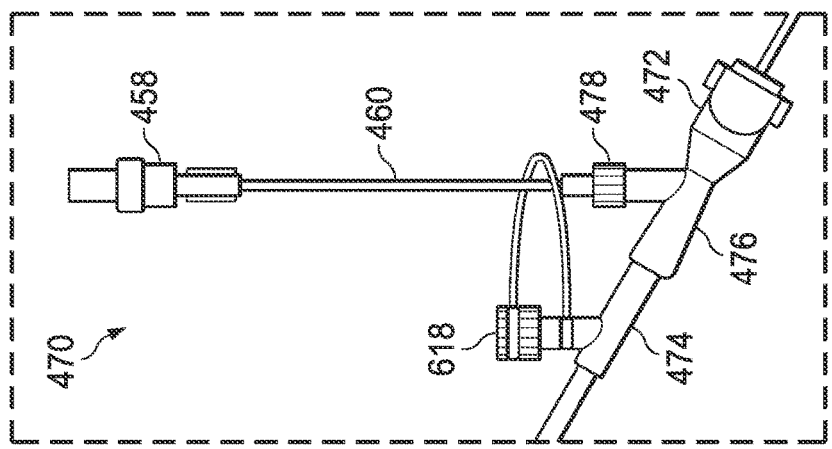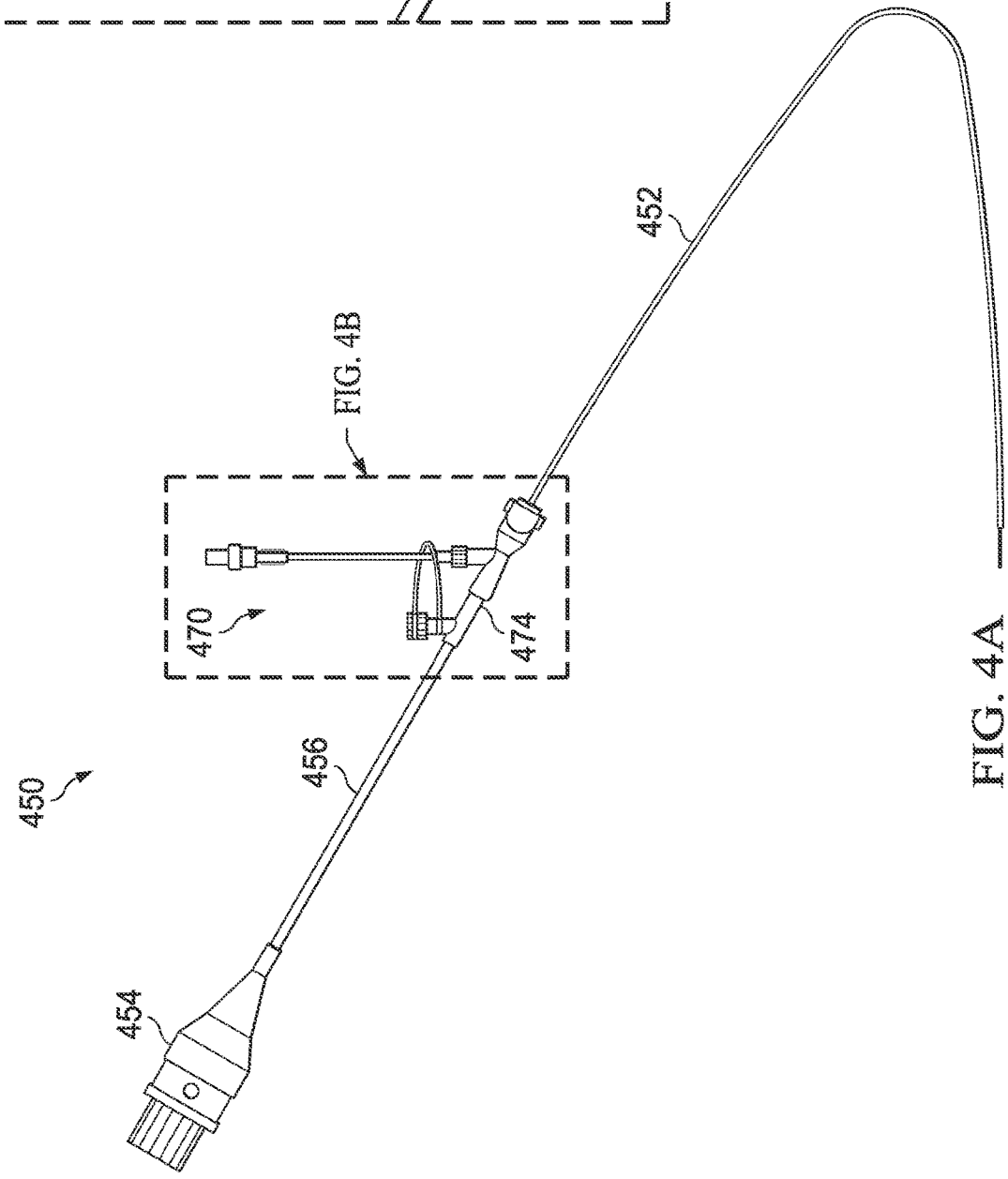

IMAGING SYSTEMS AND METHODS OF USE

CROSS-REFERENCE TO RELATED APPLICATIONS

This patent application is a continuation of U.S. patent application Ser. No. 16/955,246, filed Jun. 18, 2020, which is the U.S. national phase of International Application No. PCT/US2018/054586, filed Oct. 5, 2018, which designated the U.S. and claims priority to and the benefit of the filing date of U.S. Provisional Application No. 62/607,769, filed Dec. 19, 2017, all of which are incorporated by reference in their entirety.

FIELD

The present disclosure is directed to minimally invasive imaging systems and methods of use.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions, an operator may insert minimally invasive medical tools to reach a target tissue location, Minimally invasive medical tools include instruments such as therapeutic, diagnostic, biopsy, and surgical instruments. Minimally invasive medical tools may also include imaging instruments such as endoscopic instruments, Imaging instruments provide a user with a field of view within the patient anatomy. Some minimally invasive medical tools and imaging instruments may be teleoperated or otherwise computer-assisted. Various features may improve the effectiveness of minimally invasive imaging instruments including instrument orientation cues, heat dissipation features, and leak testing features.

SUMMARY

The embodiments of the invention are best summarized by the claims that follow the description.

Consistent with some embodiments, an imaging instrument comprises an elongate flexible shaft, a camera disposed at a distal end of the elongate flexible shaft, and a housing coupled to a proximal end of the elongate flexible shaft. The instrument also includes a light emitting diode (LED) within the housing and a heat dissipation system in thermal communication with the LED to transfer heat produced by the LED away from the housing.

Consistent with some embodiments, a system comprises a catheter including a wall having an inner surface defining a main lumen and a device including an elongate flexible shaft configured to be slideably inserted within the catheter main lumen. A structure is disposed around an outer surface of the elongate flexible shaft. The structure is configured to engage with a plurality of flat surfaces comprising a portion of the inner surface to prevent rotation of the device within the main lumen.

Consistent with some embodiments, a method comprises inserting a device into a main lumen of a catheter. The device includes a flexible shaft and a first structure disposed around an outer surface of the flexible shaft. The method also includes mating a shape of a portion of an inner wall of the main lumen of the catheter with the first structure disposed around the outer surface of the flexible shaft to prevent rotation of the flexible shaft relative to the catheter.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

FIG. 4A illustrates an imaging system according to some embodiments

FIG. 4B illustrates an imaging coupler of FIG. 4A.

Figure 1:
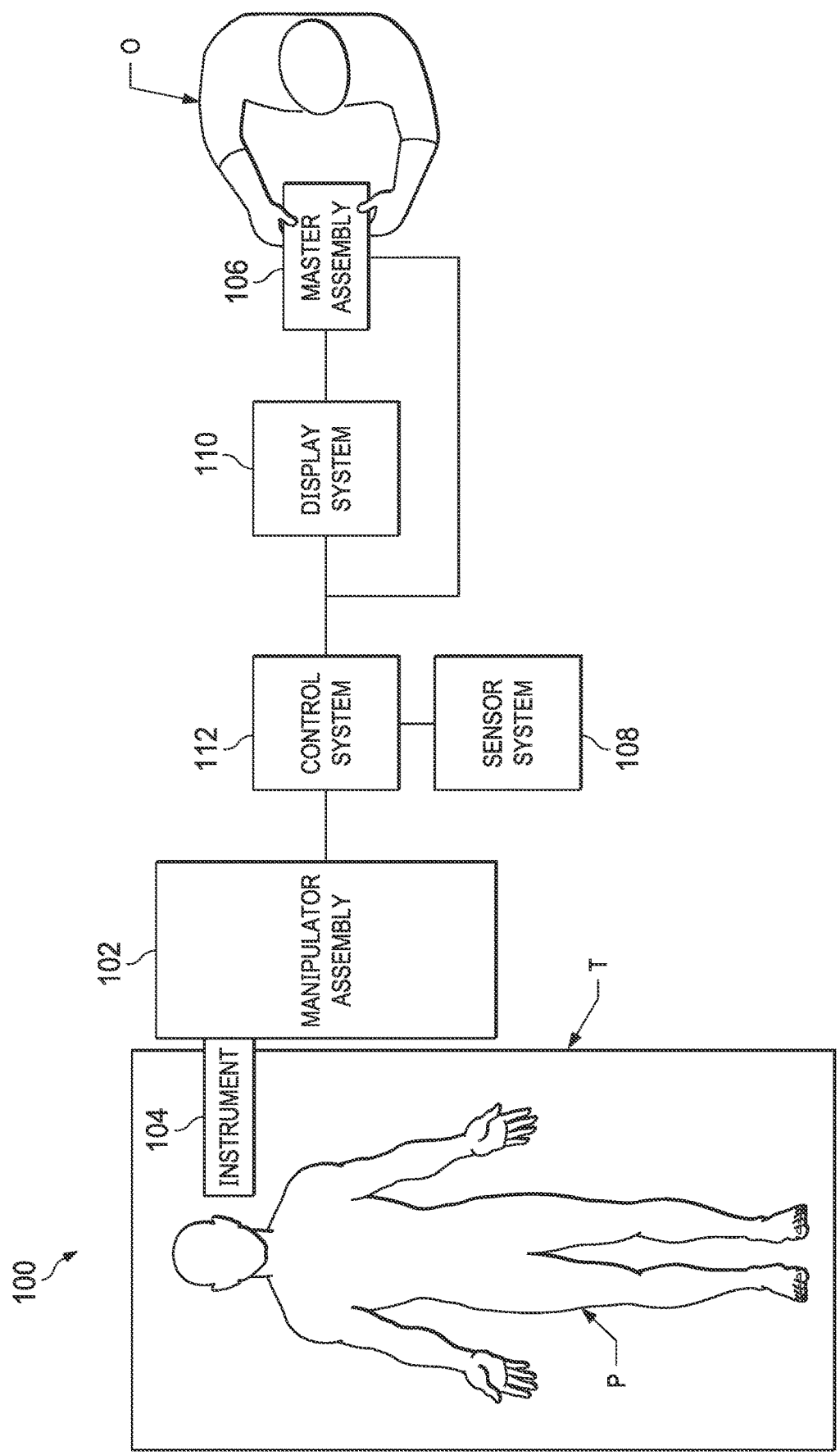
FIG. 1 is a simplified diagram of a teleoperated medical system according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. While some embodiments are provided herein with respect to such procedures, any reference to medical or surgical instruments and medical or surgical methods is non-limiting. The systems, instruments, and methods described herein may be used for animals, human cadavers, animal cadavers, portions of human or animal anatomy, non-surgical diagnosis, as well as for industrial systems and general robotic or teleoperational systems.

As shown in FIG. 1, medical system 100 generally includes a manipulator assembly 102 for operating a medical instrument 104 in performing various procedures on a patient P positioned on a table T. The manipulator assembly 102 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. Master assembly 106 generally includes one or more control devices for controlling manipulator assembly 102. Manipulator assembly 102 supports medical instrument 104 and may optionally include a plurality of actuators or motors that drive inputs on medical instrument 104 in response to commands from a control system 112. The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 also includes a display system 110 for displaying an image or representation of the surgical site and medical instrument 104 generated by subsystems of sensor system 108. Display system 110 and master assembly 106 may be oriented so operator O can control medical instrument 104 and master assembly 106 with the perception of telepresence.

In some embodiments, medical instrument 104 may include components of an imaging system (discussed in more detail below), which may include an imaging scope assembly or imaging instrument that records a concurrent or real-time image of a surgical site and provides the image to the operator or operator O through one or more displays of medical system 100, such as one or more displays of display system 110. The concurrent image may be, for example, a two or three-dimensional image captured by an imaging instrument positioned within the surgical site. In some embodiments, the imaging system includes endoscopic imaging instrument components that may be integrally or removably coupled to medical instrument 104. However, in some embodiments, a separate endoscope, attached to a separate manipulator assembly may be used with medical instrument 104 to image the surgical site. In some examples, as described in detail below, the imaging instrument alone or in combination with other components of the medical instrument 104 may include one or more mechanisms for cleaning one or more lenses of the imaging instrument when the one or more lenses become partially and/or fully obscured by fluids and/or other materials encountered by the distal end of the imaging instrument. In some examples, the one or more cleaning mechanisms may optionally include an air and/or other gas delivery system that is usable to emit a puff of air and/or other gasses to blow the one or more lenses clean. Examples of the one or more cleaning mechanisms are discussed in more detail in international Publication No. WO/2016/025465 filed Aug. 11, 2016 disclosing "Systems and Methods for Cleaning an Endoscopic Instrument"; U.S. patent application Ser. No. 15/508,923 filed Mar. 5, 2017 disclosing "Devices, Systems, and Methods Using Mating Catheter Tips and Tools"; and U.S. patent application Ser. No. 15/503,589 filed Feb. 13, 2017 disclosing "Systems and Methods for Cleaning an Endoscopic Instrument," each of which is incorporated by reference herein in its entirety. The imaging system may be implemented as hardware, firmware, software or a combination thereof which interact with or are otherwise executed by one or more computer processors, which may include the processors of the control system 112.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110.

Control system 112 may optionally further include a virtual visualization system to provide navigation assistance to operator O when controlling medical instrument 104 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRC), fluoroscopy, thermography, ultrasound, optical coherence tomography (OCT), thermal imaging, impedance imaging, laser imaging, nanotube X-ray imaging, and/or the like.

Figures 2A, 2B:
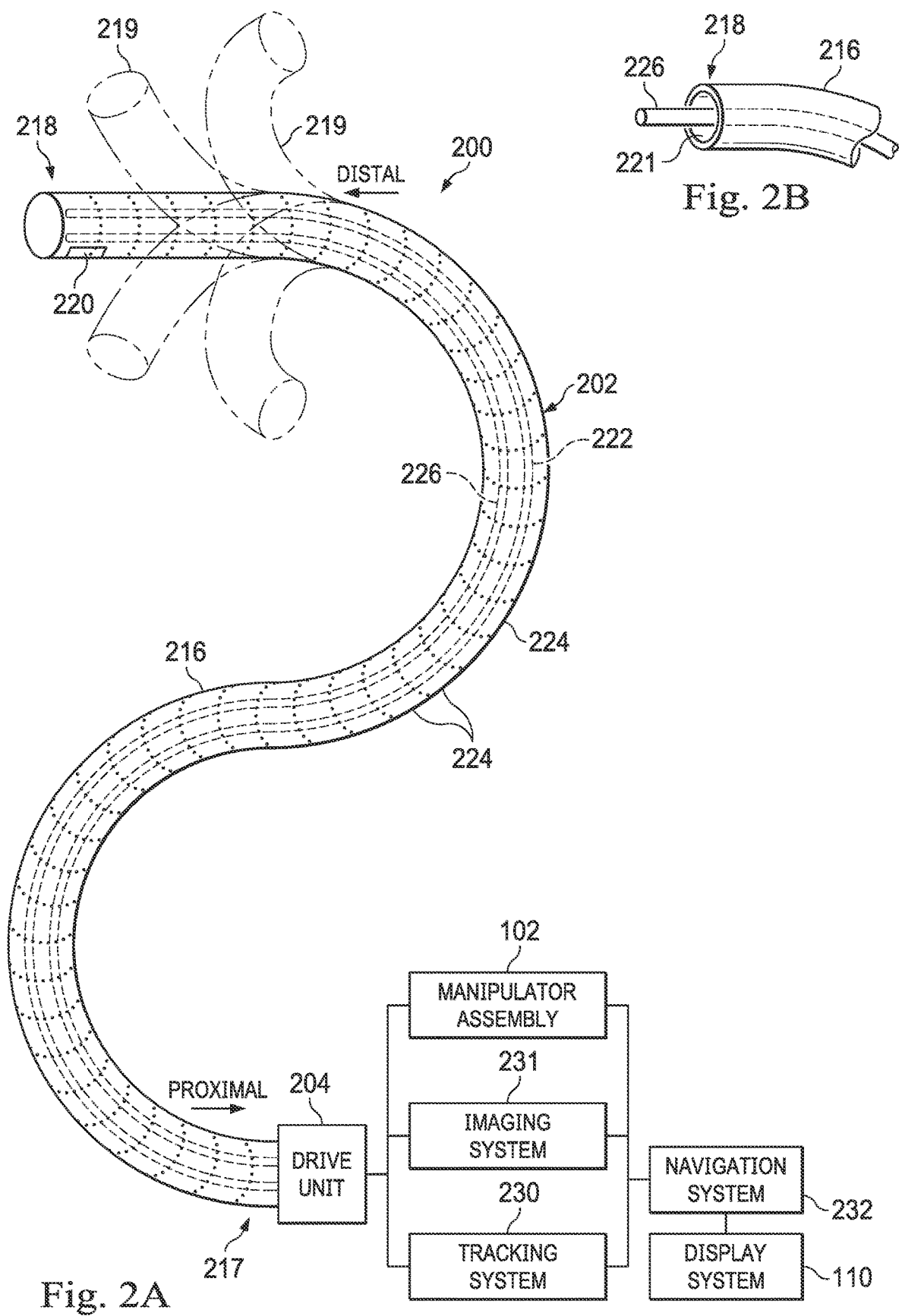
FIG. 2A is a simplified diagram of a medical instrument system according to some embodiments.
FIG. 2B is a simplified diagram of a medical instrument with an extended medical tool according to some embodiments.

FIG. 2A is a simplified diagram of a medical instrument system 200 according to some embodiments. Medical instrument system 200 includes elongate device 202, such as a flexible catheter, coupled to a drive unit 204. Elongate device 202 includes a flexible body 216 having proximal end 217 and distal end or tip portion 218. Medical instrument system 200 further includes a tracking system 230 for determining the position, orientation, speed, velocity, pose, and/or shape of distal end 218 and/or of one or more segments 224 along flexible body 216 using one or more sensors and/or imaging devices as described in further detail below.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of the elongate device may be determined using other techniques. For example, a history of the distal end pose of flexible body 216 can be used to reconstruct the shape of flexible body 216 over the interval of time. In some embodiments, tracking system 230 may optionally and/or additionally track distal end 218 using a position sensor system 220. Position sensor system 220 may be a component of an EM sensor system with position sensor system 220 including one or more conductive coils that may be subjected to an externally generated electromagnetic field. Each coil of the EM sensor system then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

Flexible body 216 includes a channel 221 sized and shaped to receive a medical instrument 226. FIG. 2B is a simplified diagram of flexible body 216 with medical instrument 226 extended according to some embodiments. In some embodiments, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical instrument 226 may be used with an imaging instrument (e.g., an image capture probe) also within flexible body 216. The imaging instrument may include a cable coupled to the camera for transmitting the captured image data. In some examples, the imaging instrument may be a fiber-optic bundle, such as a fiberscope, that couples to image processing system 231. The imaging instrument may be single or multi-spectral, for example capturing image data in one or more of the visible, infrared, and/or ultraviolet spectrums. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 281. Steerable elongate devices are described in detail in U.S. patent application Ser. No. 13/274,208 (filed Oct. 14, 2011) (disclosing "Catheter with Removable Vision Probe"), which is incorporated by reference herein in its entirety.

The information from tracking system 230 may be sent to a navigation system 232 where it is combined with information from image processing system 231 and/or the preoperatively obtained models to provide the operator with real-time position information. In some examples, the real-time position information may be displayed on display system 110 of FIG. 1 for use in the control of medical instrument system 200. In some examples, control system 116 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments, manipulator assembly 102 of FIG. 1 may be replaced by direct operator control. In some examples, the direct operator control may include various handles and operator interfaces for hand-held operation of the instrument.

Figure 3:
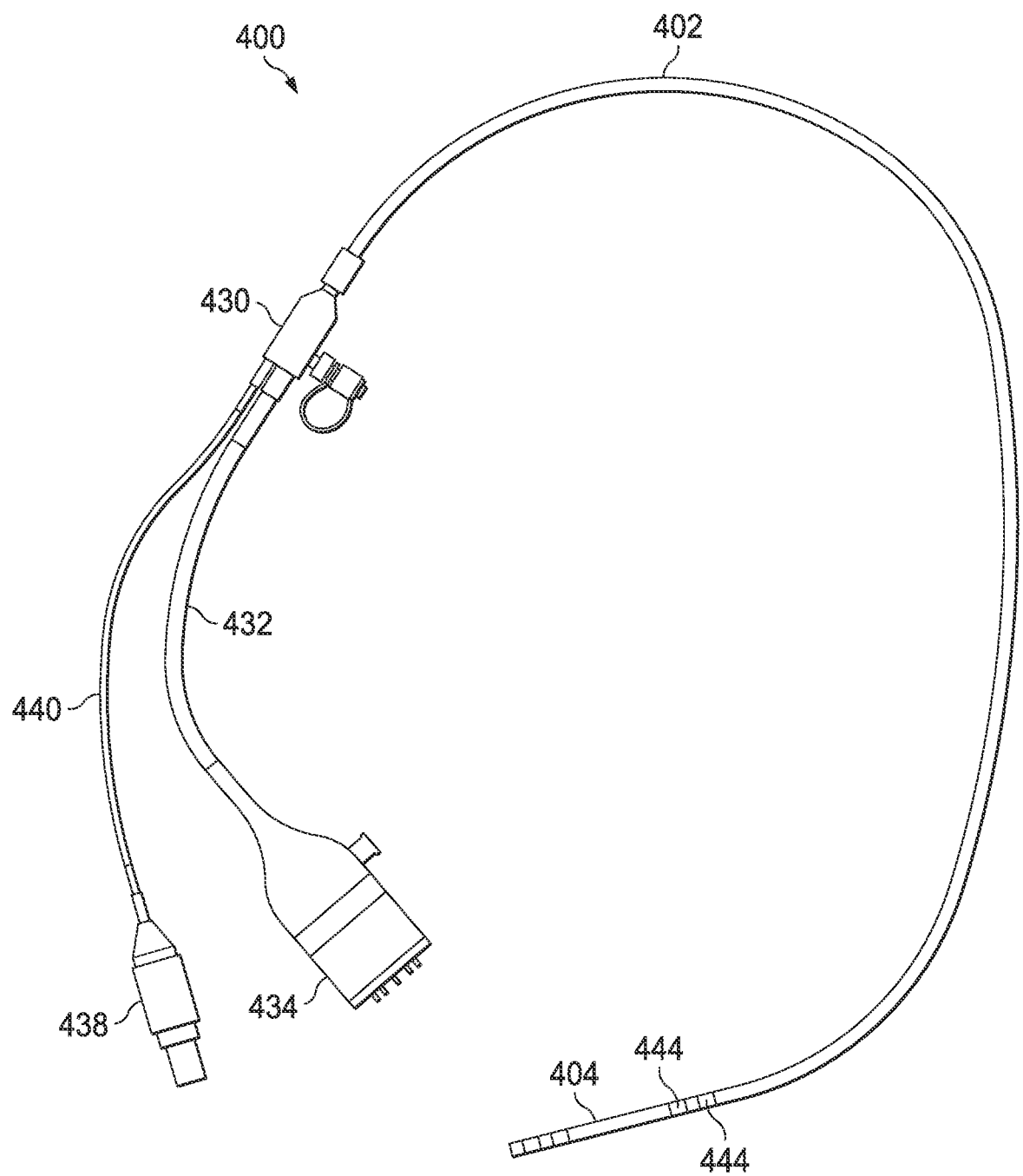
FIG. 3 illustrates an imaging system according to some embodiments.
Figure 6:
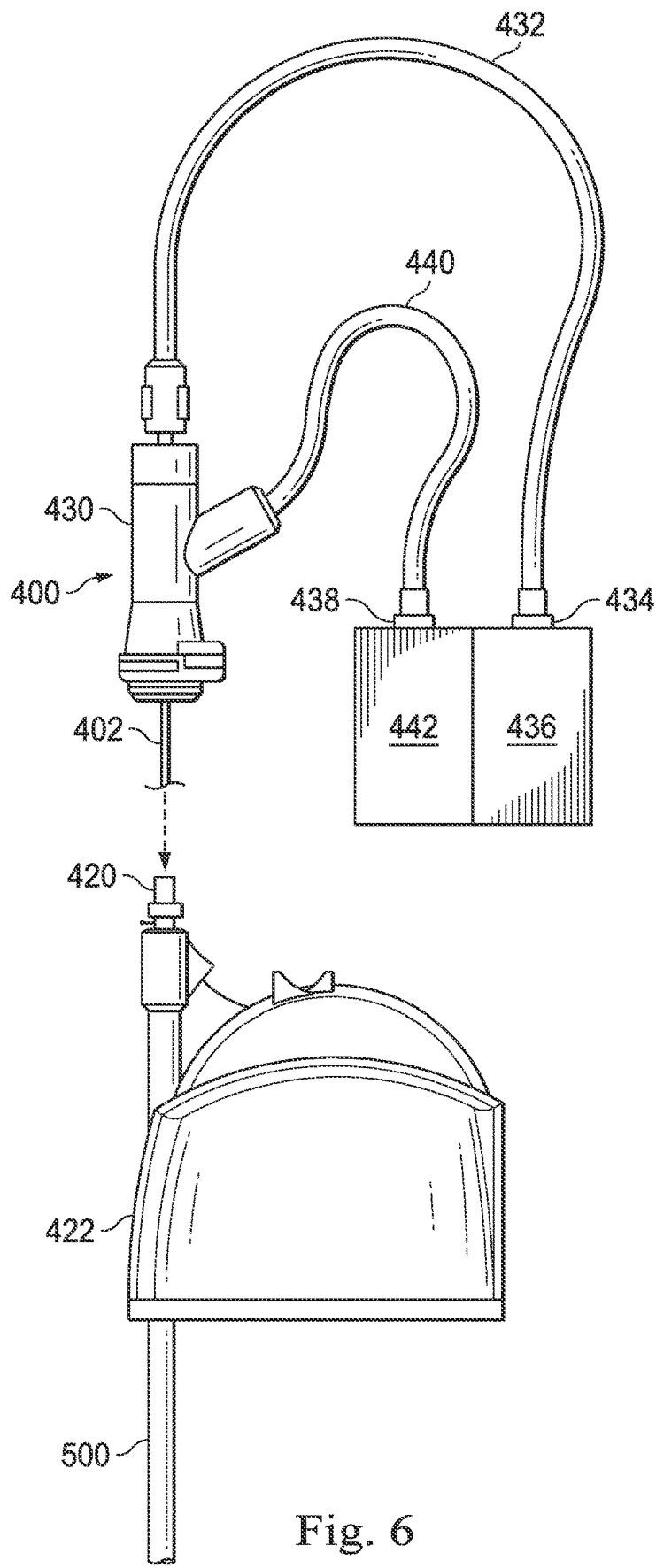
FIG. 6 illustrates an interface between an imaging system and a catheter system according to some embodiments.

FIG. 3 illustrates an example of an imaging instrument 400 that may be delivered into an anatomy through a catheter (e.g., elongate device 202). The instrument 400 includes an elongate flexible shaft 402 coupled at a distal end to a rigid or semi-rigid tubular portion 404. The elongate flexible shaft 402 may include a long, hollow tube reinforced with steel wire braiding and enclosed within plastic which can be treated by a reflow process. A proximal end of the elongate flexible shaft 402 is coupled to an imaging coupler 430 which may also be known as a vision probe adapter. A cable 432 connects the imaging coupler 430 to an imaging system adapter 434. The imaging system adapter 434 couples to image processing system 436 (e.g. image processing system 231) as shown in FIG. 6. A fluid system adapter 438 is coupled to the imaging coupler 430 by tubing 440. The fluid system adapter 438 couples to a fluid delivery-system 442 that may be used for camera cleaning, as shown in FIG. 6. In one embodiment, fluid delivery system includes a system of pumps and valves, providing for automatic, semi-automated, or user actuated for camera cleaning. In an alternative embodiment, fluid delivery system includes a manually operated fluid device (e.g. syringe) which is inserted through fluid system adapter 438 and tubing 440 for camera cleaning. The fluid system adapter 438, tubing 440, and/or imaging coupler 430 may include a set of seals or a leer-activated valve to provide for fluid flow distally and preventing leakage of fluid from the fluid system adapter. Various camera cleaning systems are disclosed, for example at PCI Publication WO2016/025465, published Feb. 18, 2016, disclosing "Systems and Methods for Cleaning an Endoscopic Instrument," PCT Publication WO2016/040128, published Mar. 17, 2016, disclosing "Devices, Systems, and Methods Using Mating Catheter Tips and Tools," and U.S. Provisional Application 62/585,922 disclosing "Systems and Methods for Cleaning Endoscopic Instruments," all of which are incorporated by reference herein in their entireties. A keying structure 444 is coupled to the elongate flexible shaft 402. In one embodiment, the keying structure 444 may be disposed along a distal portion of the shaft 402, for example, proximal of a distal steerable portion of the shaft.

FIGS. 4A and 4B illustrate an alternative example of imaging instrument 450 which may be substantially similar in structure and function as imaging instrument 400, except where described below. In a similar manner to imaging instrument 400, imaging instrument 450 can include an elongate flexible shaft 452, coupled to an imaging system adapter 454 via a cable 456, and coupled to a fluid system adapter 458 via tubing 460. However, in the embodiment of FIG. 3, it may be difficult to clean or sterilize components of the imaging instrument 400, such as the imaging coupler 430, the tubing 440, and/or the fluid system adapter 438. Thus, the imaging coupler 430 may be removeable for cleaning, sterilization, or disposal and replacement. Alternatively, as illustrated in FIGS. 4A and 4B, the imaging instrument 450 may include an imaging coupler 470. Imaging coupler 470 includes a cable adapter 474 which is coupled to cable 456. The imaging coupler 470 also includes an imaging probe adapter which includes a body 476, a connector 472, a tubing connector 478, tubing 460, and fluid system adapter 458, as described below.

A distal end of the imaging coupler 470 can include a connector 472 which allows for fast and easy removeable coupling of the cable adapter 474 to a medical device (e.g. flexible elongate device 202) as will be described in more detail below. The imaging coupler 470 can be connected to tubing 460 in a Y-type fashion. The fluid system adapter 458, tubing 460, and/or imaging coupler 470 may include a set of seals or a leer-activated valve to provide for fluid flow distally and preventing leakage of fluid from the fluid system adapter 458. A body 476 of the imaging coupler 470 can be detachable from the cable adapter 474 using a threaded attachment, a removable press fit, a magnetic coupling, and/or the like. In one embodiment the cable adapter 474 and/or imaging coupler 470 are removable from the imaging instrument 450, allowing for the cable adapter 474 or imaging coupler 470 to be separately removable for cleaning, sterilization, or disposal and replacement with a clean and/or sterile component. In some embodiments the cable adapter 474 or the imaging probe adapter may be a single use component. In an alternative embodiment, the tubing 460 and fluid system adapter 458 are removable from the body 476 at tubing connector 478, allowing the tubing 460 and fluid system adapter 458 to be additionally or alternatively removable for cleaning, sterilization, disposal and replacement.

Figure 5:
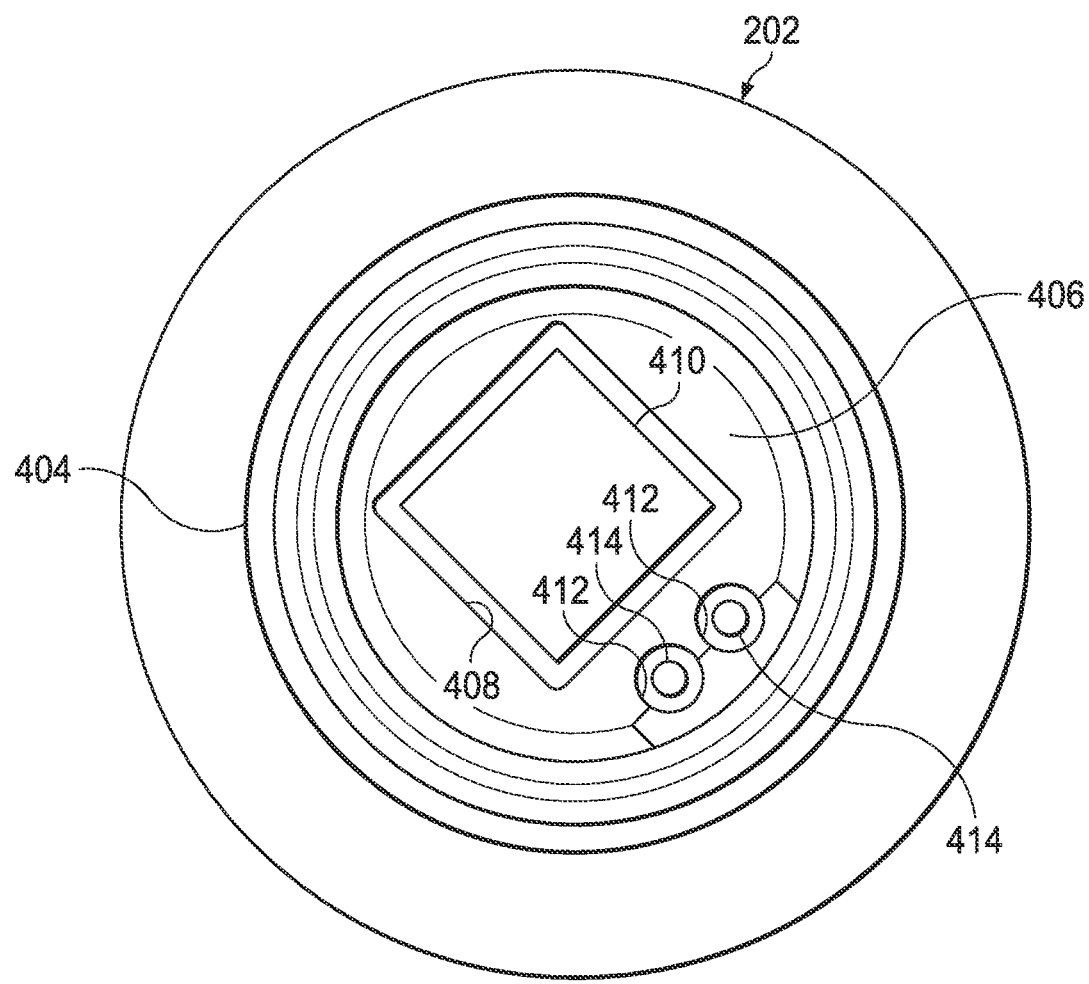
FIG. 5 illustrates a distal tip of an imaging system according to some embodiments.

FIG. 5 illustrates a distal end view of the rigid tubular portion 404. The rigid tubular portion 404 includes a distal surface 406 including an opening 408 that may be square, rectangular, or another shape suitable for use with a camera 410. The distal surface 406 also includes lumens 412 that may be circular or another shape suitable for conveying light from illumination fibers 414. The camera 410 may be bonded into the opening 408 and the fibers 414 may be bonded into the lumens 412. The rigid tubular portion 404 may be coupled to the distal end of the elongate flexible shaft 402 by thermal bonding and may include slits, flanges, or other physical features to which the melted bonding material may adhere and harden to create a strong thermal bond. In alternative embodiments, an adhesive may be used for bonding. The rigid tubular portion 404 may be formed of metal or of a plastic that is more rigid than the elongate flexible shaft. In some embodiments, the length of the rigid tubular portion may be approximately 8-9 mm, but a shorter length of approximately 5-6 mm may be particularly suitable for navigating tight catheter bends and reducing wear on the inner surface of the catheter. Various systems for maintaining a clear view of the patient anatomy include the use of hydrophobic coatings on the sensor 410 or other camera cleaning systems.

FIG. 6 illustrates an example of an interface coupling the imaging instrument 400 to the image processing system 436 and to a catheter 500 (e.g., elongate device 202) according to some embodiments. The image processing system 436 (e.g. image processing system 231) may be coupled to the imaging instrument 400 via imaging system adapter 434 as shown in FIG. 6. Catheter 500 may be coupled at a catheter proximal portion to a catheter housing 422 which can include a catheter port 420. The flexible elongate shaft 402 of imaging instrument 400 can be extended first through a port lumen in catheter port 420, then through a catheter lumen in catheter 500 until the imaging coupler 430 is fixedly coupled to a catheter port 420. The elongate flexible shaft 402 extending through the catheter 500 may be communicatively coupled to processors of the image processing system 436 by the cabling 432 that conveys power, image data, instruction signals or the like. The imaging coupler 430 can also couple the fluid delivery system 442 to the proximal end of the catheter 500 through coupler 430 and catheter port 420. In alternative embodiments, illustrated in FIGS. 4A and 4B, imaging processing system 436 may be coupled to imaging instrument 450 via cable adapter 474 and imaging coupler 470. Imaging coupler 470 may include a connector 472 (e.g. a quick connect key) which engages and release the catheter port 420.

Figure 7A:
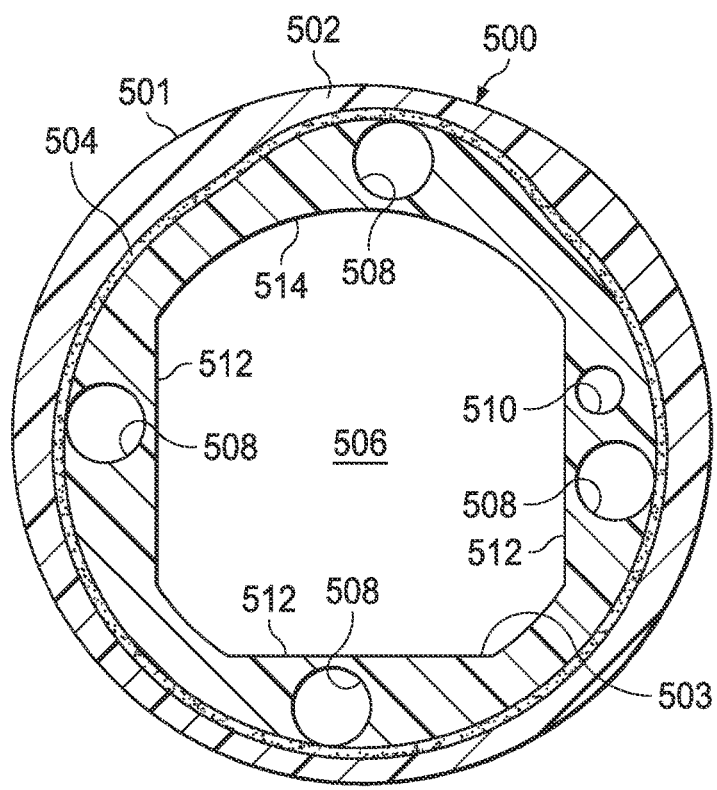
FIG. 7A is a cross-sectional view of an elongated member of an imaging system according to some embodiments.

FIG. 7A illustrates a cross-sectional view of the catheter 500 according to one embodiment. The catheter 500 includes a catheter body 502 having a wall with an outer surface 501 and an inner surface 503, the inner surface defining a main lumen or channel 506. The catheter body 502 can include a braided layer 504 that extends longitudinally down the length of the catheter to provide added strength. The braided layer 504 may be formed of various metals, for example, braided stainless steel wire, and/or polymer materials. Additional reinforcement layers may surround the main lumen 506 extending longitudinally through the catheter 500. A plurality of secondary lumens can include lumens 508 which extend through the catheter body 502 to define passageways for steering members such as control wires and lumen 510 which extends through the catheter body 502 to define a passageway for a sensor such as an optical fiber shape sensor. In the embodiment of FIG. 7A, the braided layer 504 surrounds the channels 508, 510, but in other embodiments one or more braided layers may be located inward, toward the inner surface 503. In this embodiment, a portion of the inner surface 503 has a profile defining a shape for a portion of the main lumen, the shape having three flat surfaces 512 and a curved surface 514, forming a "bread slice" shape. The remaining length of the inner surface of the catheter wall can have a substantially circular shape defining a substantially circular main lumen along the remaining length of the catheter. In alternative embodiments, the full length of the inner surface of the catheter, and thus the full length of the main lumen, may include the profile of FIG. 7A.

Figure 7B:
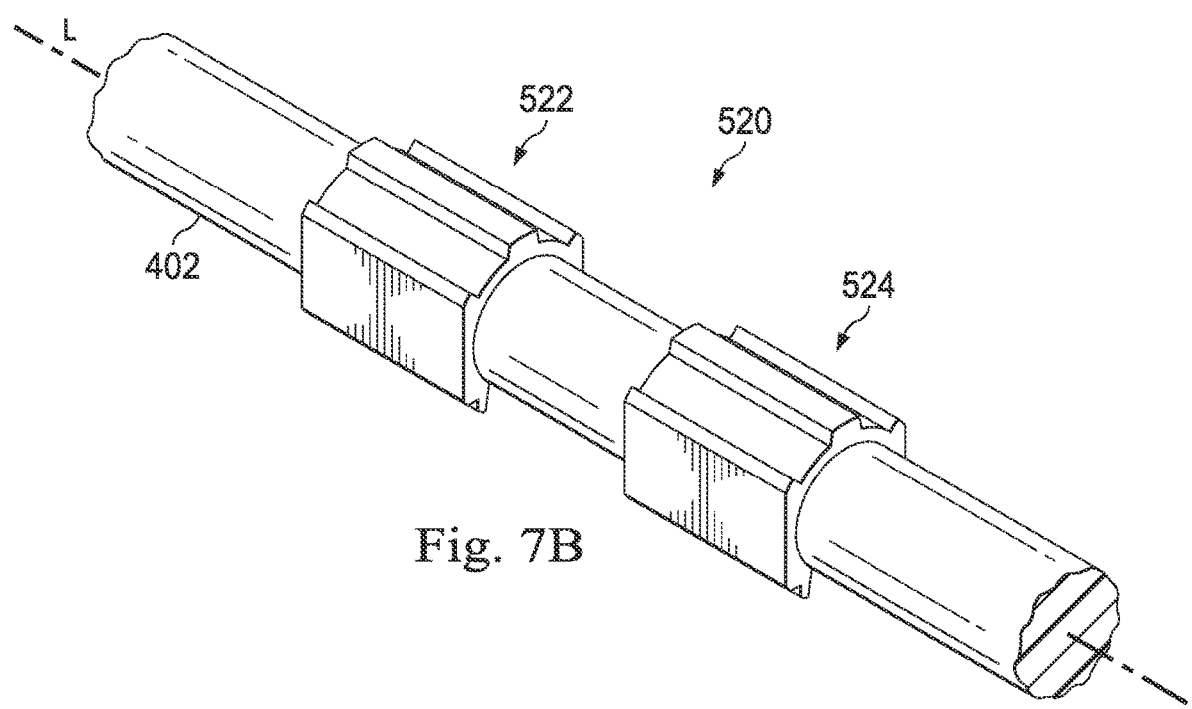
FIG. 7B illustrates a keying structure for use with the elongated member of FIG. 7A.

FIG. 7B illustrates a keying structure 520 fixedly coupled to elongate flexible shaft 402, for use with the catheter 500 to maintain a fixed orientation (about a longitudinal axis L) of the elongate flexible shaft 402 relative to the catheter 500, and more specifically to maintain a fixed orientation of the camera 410 relative to the catheter. In this embodiment, the keying structure 520 includes a key portion 522 spaced longitudinally apart from a key portion 524, with both key portions bonded to the outer wall of the shaft 402. Both key portions are substantially identical in shape, but the redundancy may be beneficial to provide greater resistance to twist and may be beneficial if one of the key portions comes loose and is no longer able to perform the function of maintaining an orientation of the shaft relative to the catheter. In alternative embodiments, any number of key portions may be provided along a length of the elongate flexible shaft 402. In alternative embodiments, a single long key portion (not shown) may be provided to provide required roll orientation of the shaft 402 relative to the catheter 500. The long single key portion may be constructed from a very flexible material such as a low durometer polymer material which would provide for flexibility of the shaft 402 which could be desirable when steeling a catheter 500 and shaft 402 through tortuous anatomy with multiple small bends. In some embodiments, low durometer polymers could have a high coefficient of friction which would cause drag between the key portion and the inner surface 503 of catheter 500. Thus, in some embodiments, a plurality of short length key portions spaced down the length of the shaft would provide for required roll orientation of the shaft relative to the catheter, required flexibility, and low friction between the key portions and inner surface 503 of catheter 500.

Figure 7C:
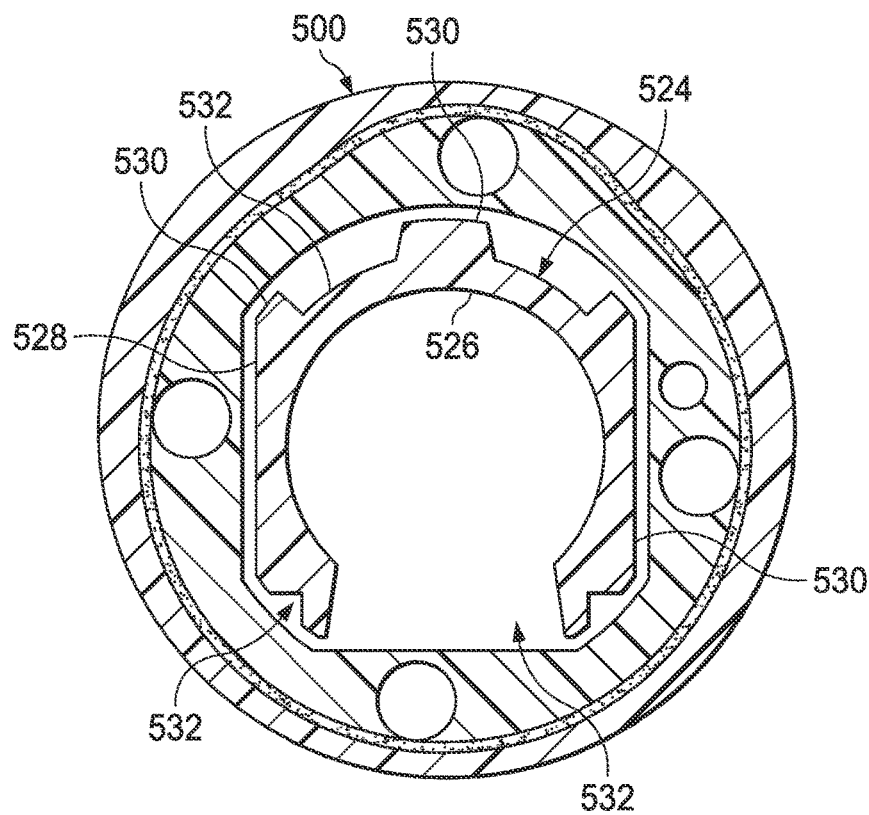
FIG. 7C illustrates a cross-sectional view of the keying structure of FIG. 7B.

FIG. 7C illustrates a cross-sectional view of the key portion 524 which may be identical in construction to key portion 522. The key portion 524 may be a polymer or metal sleeve member with an inner wall 526 corresponding to a profile of an outer surface of the elongate flexible shaft 402. In this embodiment the inner wall 526 is generally circular, but in alternative embodiments, the inner wall may be U-shaped. An outer profile 528 of the key portion 524 is sized and shaped to pass (e.g., slidingly) through the main lumen 506 of the catheter 500 while engaging with the portion of the inner surface 503 having a profile illustrated in FIG. 7A, preventing axial rotation of the shaft 402 and key portion 524 relative to the catheter. The outer profile 528 includes surfaces 530 which engage the inner surfaces 512, 514 of the catheter to prevent rotation. The outer profile 528 also includes recessed surfaces 532 which are offset from the inner surfaces 512, 514 of the catheter and form channels though which a fluid, such as a cleaning fluid, may pass between the catheter and the key portion 524. In this embodiment, the shaft may have a single correct orientation of insertion relative to the catheter.

Figure 8A:
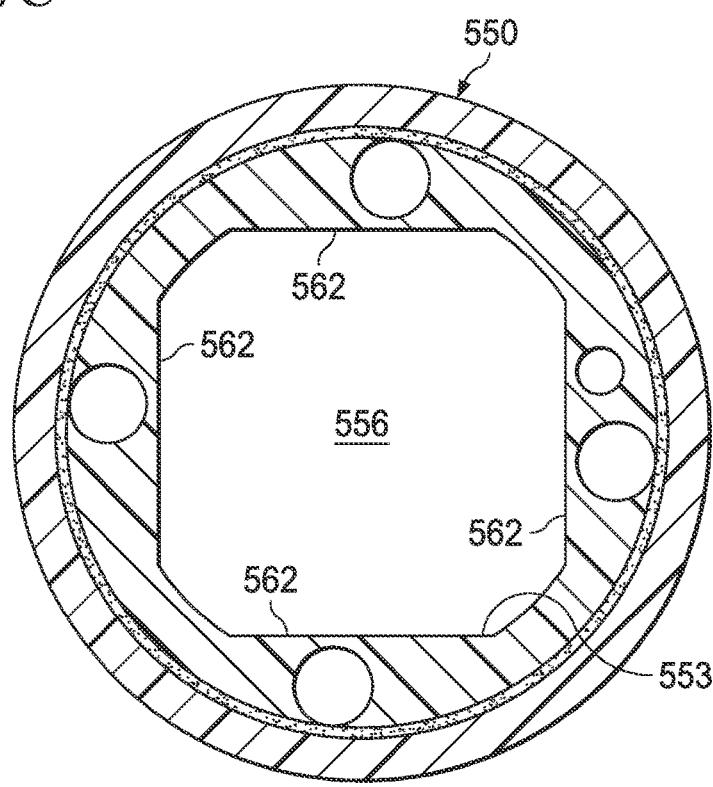
FIG. 8A is a cross-sectional view of an elongated member of an imaging system according to some embodiments.

In another embodiment, FIG. 8A illustrates a cross-sectional view of a catheter 550 (e.g., elongate device 202) similar in function and structure to catheter 500 of FIG. 7A with the exception of a shape a portion of the inner surface 553 defining main lumen 556. In this embodiment, a portion of the catheter inner surface 553 has a profile including four flat surfaces 562, forming a rounded or tapered-edge square or rectangular profile defining the shape of main lumen 556. The remaining length of the inner surface of the catheter wall can have a substantially circular shape defining a substantially circular main lumen along the remaining length of the catheter. In alternative embodiments, the full length of the inner surface of the catheter, and thus the full length of the main lumen, may include the profile of FIG. 8A. In alternative embodiments, the number of flat surfaces may be greater, creating a pentagonal, hexagonal, or octagonal profile, for example. The selected shape and number of flat surfaces (and the corresponding key shape) may be chosen to ensure that the probe does not rotate during use and can be used determine an orientation (or a limited number of potential orientations) of the probe is relative to the catheter. The "bread slice" shape of FIG. 7A provides for a single orientation of the probe and catheter. While the single option for orientation of probe relative to catheter allows for unambiguous orientation determination, it may be more difficult to arrange during installation. A square key and corresponding catheter lumen provides for four different orientations which means that additional info must be provided to determine initial orientation of probe to catheter, but with 4 different possible orientations, installation can be much easier. Other shapes can provide the same trade-offs, i.e. more walls provide for more installation orientations for easier installation but adds more possible relative orientations.

Figure 8B:
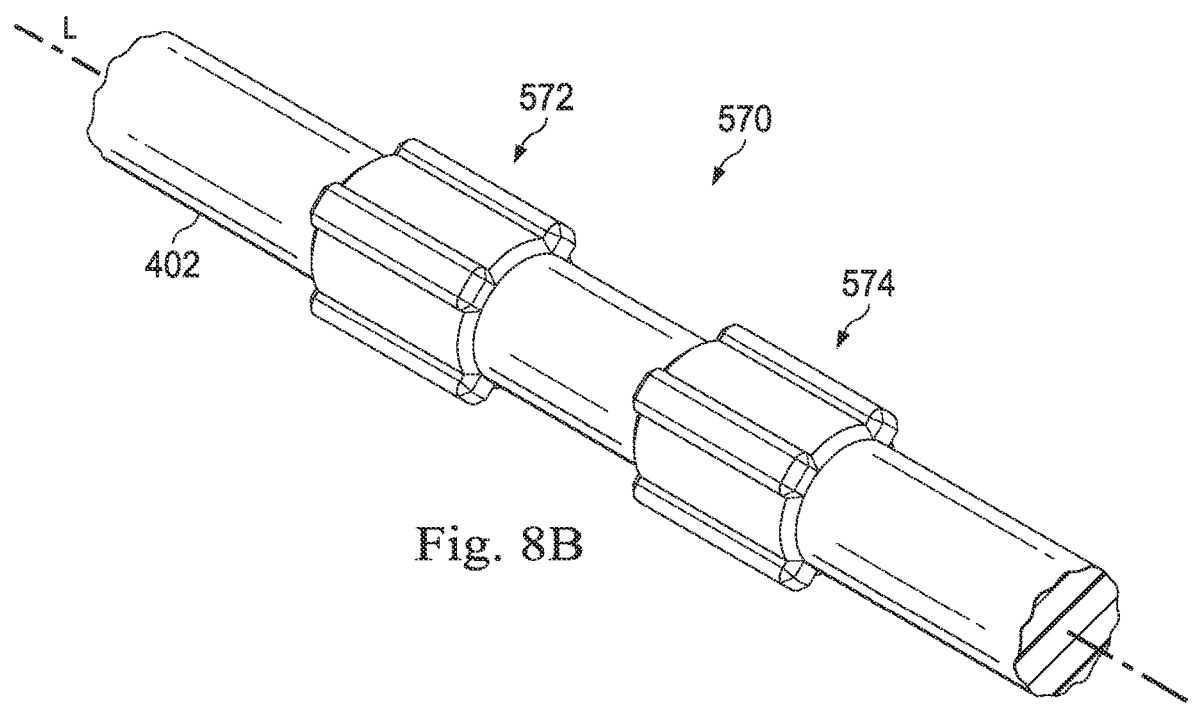
FIG. 8B illustrates a key for use with the elongated member of FIG. 8A.

FIG. 8B illustrates a keying structure 570 fixedly coupled to elongate flexible shaft 402, for use with the catheter 550 to maintain a fixed orientation (about a longitudinal axis L) of the shaft 402 relative to the catheter 550, and more specifically to maintain a fixed orientation of the camera relative to the catheter. In this embodiment, the keying structure 570 includes a key portion 572 spaced longitudinally apart from a key portion 574, with both key portions bonded to the outer wall of the shaft 402. Both key portions are substantially identical in shape, but the redundancy may be beneficial to provide greater resistance to twist and may be beneficial if one of the key portions comes loose and is no longer able to perform the function of maintaining an orientation of the shaft relative to the catheter. In alternative embodiments, a single long key portion (not shown) may be provided to provide required roll orientation of the shaft 402 relative to the catheter 500. The long single key portion may be constructed from a very flexible material such as a low durometer polymer material which would provide for flexibility of the shaft 402 which could be desirable when steering a catheter 500 and shaft 402 through tortuous anatomy with multiple small bends. In some embodiments, low durometer polymers could have a high coefficient of friction which would cause drag between the key portion and the inner surface 503 of catheter 500. Thus, in some embodiments, a plurality of short length key portions spaced down the length of the shaft would provide for required roll orientation of the shaft relative to the catheter, required flexibility, and low friction between the key portions and inner surface 503 of catheter 500.

Figure 8C:
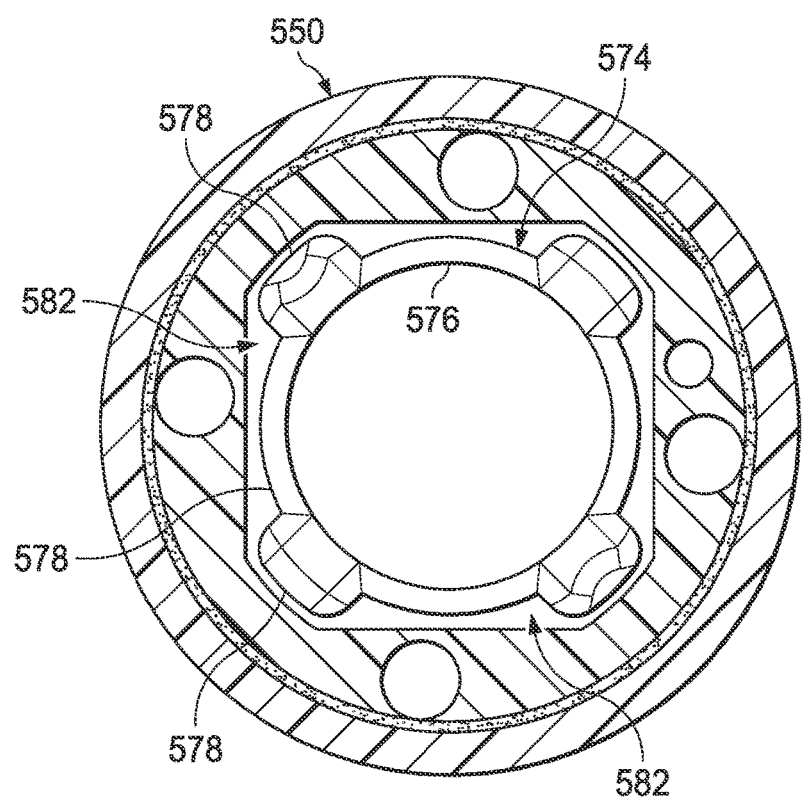
FIG. 8C illustrates a cross-sectional view of the keying structure of FIG. 8B.

FIG. 8C illustrates a cross-sectional view of the key portion 574. The key portion 574 may be a polymer or metal sleeve member with an inner wall 576 corresponding to a profile of the outer surface of the elongate flexible shaft 402. In this embodiment the key portion inner wall 576 is generally circular, but in alternative embodiments, the inner wall may be U-shaped. The outer profile 578 of the key portion 574 is sized and shaped to pass (e.g., slidingly) through the main lumen 556 of the catheter 550. In some embodiments, the outer profile 578 of the key portion 574 is configured to pass through the portion of the main lumen 556 shaped with a profile illustrated in FIG. 8A to prevent axial rotation of the shaft 402 and key portion 574 relative to the catheter. The outer profile 578 includes surfaces 580 which engage a portion of the inner surface 553 of the catheter to prevent rotation. In particular the surfaces 580 may engage the tapered edges of the inner surface 553. The outer profile 578 includes recessed surfaces 582 which are offset from the inner surfaces 562 of the catheter and form channels though which a fluid, such as a cleaning fluid, may pass between the catheter and the key portion 574. In alternative embodiments, the engagement surfaces 580 of the outer profile 578 may engage and slide along the flat surfaces 562. In this embodiment, the shaft may have four correct orientations of insertion relative to the catheter.

Figure 9:
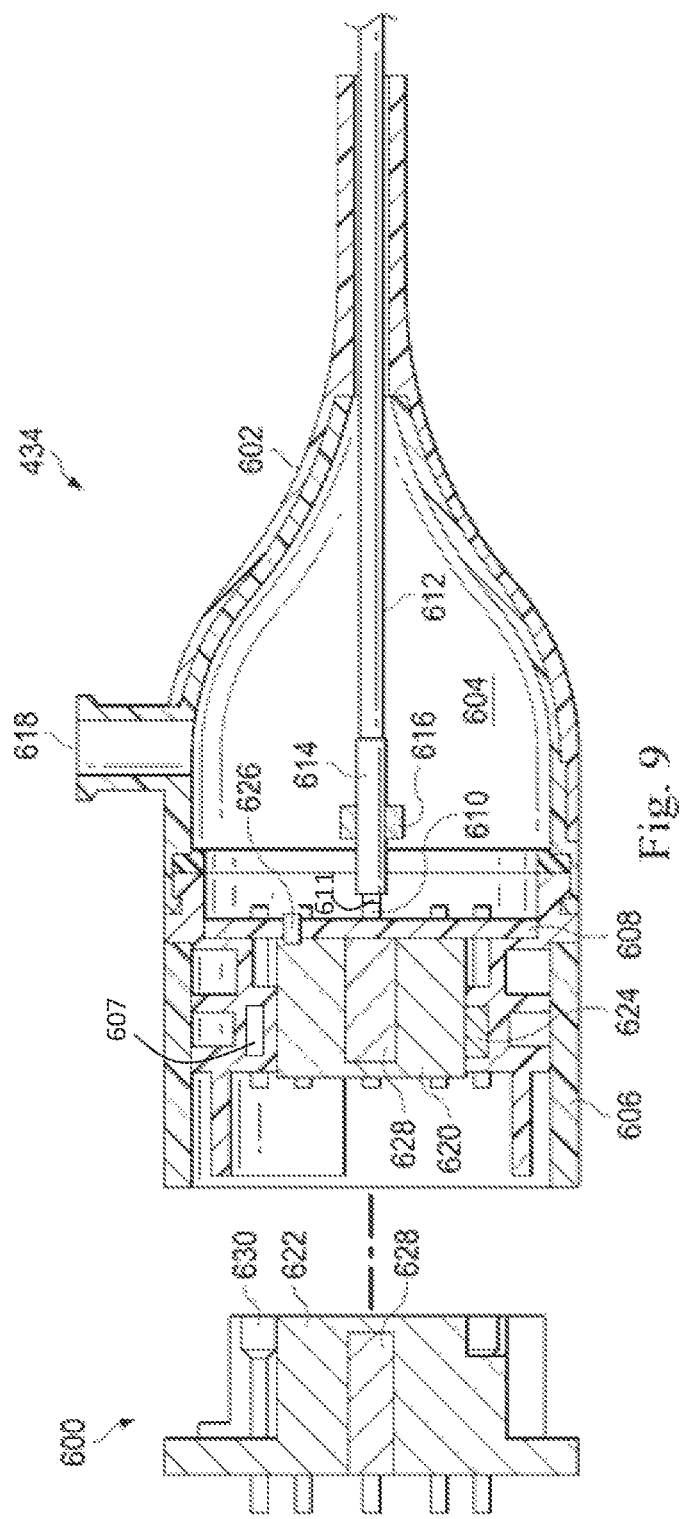
FIG. 9 illustrates a cross-sectional view of an imaging system adapter according to some embodiments.

FIG. 9 illustrates a cross-sectional view of an example of the imaging system adapter 434 according to some embodiments. The imaging system adapter 434 couples with a connector 600 which may be an interface to the image processing system 436 and/or teleoperational manipulator carriage. The imaging system adapter 434 includes a housing 602 which defines a chamber 604 and which includes a component compartment 606. The component compartment 606 houses a printed circuit board 608 to which is attached various electrical components including an illumination device such as a light emitting diode (LED) 610, memory storage devices 607, electrical power connections, resistors, capacitors, diodes and other electrical components that provide connection to the imaging system. The electrical components may, for example, control current to the LED, read and write data to the memory chips, and read and write data to and from the camera. The components in the adapter 434 may also provide identification information used to authenticate the imaging instrument 400 to the imaging system and/or the teleoperational system. The components in the adapter 434 may also include a use counter which tracks information about the number of procedures in which the imaging instrument has been used.

An optical fiber 612 is coupled at a distal end to the tip of the shaft 402. The proximal end of the optical fiber 612 extends into the chamber 604 of the housing 602 to optically couple with the LED 610. The optical coupling includes a fiber stand 614 and a ferrule assembly 616. The ferrule assembly may include a tripod to hold the fiber stand 614 in place over the LED 610. The ferrule assembly 616 may be aligned with the LED to that the LED and the fiber 612 are butt coupled. In alternative embodiments, the fiber and the LED may be bonded in place with an adhesive. Various optical components may be used to direct the light from the LED toward the optical fiber 612. Suitable optical components may include lenses 611 or filters. A ball lens, for example, may be used to collect light from the LED and direct it toward the optical fiber 612. The component compartment 606 may be sealed from the chamber 604.

Referring back to FIGS. 4A, 5, and 9, camera 410 can be bonded to the distal surface 406 positioned near a distal end of elongate flexible shaft 452. Electrical cables can run from the camera 410, through a working lumen (not shown) in elongate flexible shaft 452, through a cavity of the cable adapter 474, terminating at imaging system adapter 454/434 within chamber 604. The working lumen, cavity of the cable adapter 474, and chamber 604 can be in fluid communication along a fluid path and sealed from leakage outside of imaging instrument 450. Thus, a port used for leak testing can be positioned at any location along the fluid path of the imaging instrument 450. The port may be provided to pressurize an enclosed area (e.g. chamber 604, the cavity of cable adapter 474, or a lumen of cable 456 or elongate flexible shaft 452) and test for leakage, for example an imaging instrument such as imaging instrument 400 may be submerged in a fluid and the port may be used to flush the imaging instrument with air such that any leak in lining of the imaging instrument would be evident from air escape as bubbles in the fluid.

In one example, the imaging system adapter 434 can include a leak test port (e.g. leak test port 618 of FIG. 9), which can be integrated, e.g. molded, glued, or otherwise fixedly attached. In another example, the cable adapter 474 can include the leak test port 618, which can be integrated, e.g. molded, glued, or otherwise fixedly attached, as illustrated in FIGS. 4A and 4B.

Heat generated by the LED 610 may be dissipated or thermally communicated through a variety of heat dissipation systems and techniques. The component compartment 606 may include a thermal pad such as a heat transfer pad 620 which interfaces with a heat transfer pad 622 in the connector 600. Heat generated from the LED 610 may flow through the heat transfer pad 620, into the heat transfer pad 622, and may be dissipated over the imaging system, the teleoperational manipulator carriage, or any system to which the connector 600 is coupled. The heat transfer pads 620, 622 may be formed from aluminum blocks. The heat transfer pad 620 may be thermally coupled to the LED 610 and board 608 with heat sink grease. A heat dissipation system may also include a cooling system 624. A cooling system 624 may include passive cooling elements such as fins or active cooling elements to provide cooling fluid flow. Active cooling elements may include a fluid circulation system including pipes, piping systems, pumps, and controls to circulate a fluid coolant; fans; heat sinks; or combinations of multiple cooling elements. A temperature sensor 626 may be positioned near the board 608 to monitor the temperature. The measured temperature from the sensor 626 may be used to control the current to the LED 610. For example, if the measured temperature exceeds a threshold value, the current to the LED may be reduced. In some embodiments including a cooling system 624, heat transfer pad 622 may be omitted along with magnets or other components utilized for making good thermal contact with pad 620.

The connector 600 may be biased toward contact with the adapter 434 with biasing elements. For example, magnets 628 may be one type of biasing element that pulls the pads 622, 620 together to promote direct heat transfer. Alternately, a magnet may be on one side and a piece of ferromagnetic material such as a steel plug on the other side. Magnets may either be permanent magnets or electromagnets. Another type of biasing element may be one or more spring-loaded pins 630 that exert a force on the adapter 434, to promote heat transfer and to urge the imaging instrument 400 toward the distal end of the catheter 500.

In various alternative embodiments, multiple illumination devices may be used, including multiple LEDs. Multiple LEDs may be affixed to a common printed circuit board. In various alternative embodiments, multiple optical fibers may transmit light and information between the imaging system and the camera. For example, two fibers may be coupled side-by-side to a single LED. In various embodiments, slack in the optical fiber 612 or in the fiber coupling components may allow for bending and stretching of the fiber during a procedure. In various embodiments, a blue LED with a phosphor coating may be used to create a white LED. In various embodiments, one of the optical components used with the optical fiber may be a polarizer to minimize hot spots.

One or more elements in embodiments of the invention may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A system comprising:
   a catheter including a wall having an inner surface defining a main lumen; and
   a device including:
      an elongate flexible shaft configured to be slideably inserted within the main lumen; and
      a structure coupled to an outer surface of the elongate flexible shaft, wherein the structure is configured to engage with a plurality of flat surfaces comprising a portion of the inner surface to prevent rotation of the elongate flexible shaft within the main lumen, wherein the structure includes an inner wall that engages with a portion of the outer surface of the elongate flexible shaft, the inner wall having a shape that makes up a portion of a circle.

2. The system of claim 1, wherein the device is an imaging device.

3. The system of claim 1, wherein the structure comprises a first key portion and a second key portion, the second key portion being spaced apart from the first key portion along a longitudinal axis of the elongate flexible shaft.

4. The system of claim 1, wherein the portion of the inner surface includes at least three flat surfaces and an outer profile of the structure includes two non-adjacent surfaces configured to slide along two of the at least three flat surfaces of the portion of the inner surface.

5. The system of claim 1, wherein:
   the portion of the inner surface of the wall includes four flat surfaces; and
   an outer profile of the structure includes at least four surfaces, including two non-adjacent surfaces, configured to slide along and engage with the four flat surfaces of the portion of the inner surface.

6. The system of claim 1, wherein:
   the portion of the inner surface includes a first curved surface extending between two of at least three flat surfaces; and
   an outer profile of the structure includes a second curved surface arranged between two non-adjacent surfaces.

7. The system of claim 1, further comprising:
   an imaging coupler coupled to the elongate flexible shaft for coupling the device to the catheter, wherein the imaging coupler is removable from the elongate flexible shaft.

8. The system of claim 7, wherein the imaging coupler is disposable after a single use.

9. The system of claim 7, wherein the imaging coupler includes a cable adapter for coupling the imaging coupler to an imaging cable.

10. The system of claim 9, wherein the cable adapter includes a leak test port.

11. The system of claim 1, wherein the structure is coupled to the outer surface of the elongate flexible shaft by a bonding material.

12. The system of claim 1, wherein the structure is an elongate flexible structure that bends with the elongate flexible shaft.

13. A system comprising:
   a catheter including a wall having an inner surface defining a main lumen; and
   a device including:
      an elongate flexible shaft configured to be slideably inserted within the main lumen; and
      a structure coupled to an outer surface of the elongate flexible shaft, wherein the structure is configured to engage with a plurality of flat surfaces comprising a portion of the inner surface to prevent rotation of the elongate flexible shaft within the main lumen, wherein the portion of the inner surface includes at least three flat surfaces and an outer profile of the structure includes two non-adjacent surfaces configured to slide along two of the at least three flat surfaces of the portion of the inner surface, and wherein the outer profile of the structure includes a recessed surface between the two non-adjacent surfaces, the recessed surface of the outer profile of the structure and the inner surface of the catheter forming a fluid channel.

14. A system comprising:

a catheter including a wall having an inner surface defining a main lumen; and a device including:

an elongate flexible shaft configured to be slideably inserted within the main lumen; and a structure coupled to an outer surface of the elongate flexible shaft, wherein the structure is configured to engage with a plurality of flat surfaces comprising a portion of the inner surface to prevent rotation of the elongate flexible shaft within the main lumen, wherein the structure includes a U-shaped inner wall that engages with a portion of the outer surface of the elongate flexible shaft.

\* \* \* \* \*

UNITED STATES PATENT AND TRADEMARK OFFICE
CERTIFICATE OF CORRECTION

PATENT NO. : 12,268,361 B2  
APPLICATION NO. : 17/943516  
DATED : April 8, 2025  
INVENTOR(S) : Andrew J. Hazelton et al.

Page 1 of 1

It is certified that error appears in the above-identified patent and that said Letters Patent is hereby corrected as shown below:

In the Specification

Column 5, Line 4, change "(MRC)" to -- (MRI) --

Column 7, Line 22, change "leer-activated" to -- luer-activated --

Column 7, Line 25, change "PCI" to -- PCT --

Column 7, Line 65, change "leer-activated" to -- luer-activated --

Column 9, Line 50, change "steeling" to -- steering --

Signed and Sealed this  
Thirteenth Day of May, 2025

Coke Morgan Stewart  
*Acting Director of the United States Patent and Trademark Office*